US012497620B2

(12) United States Patent
Thompson

(10) Patent No.: US 12,497,620 B2
(45) Date of Patent: Dec. 16, 2025

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/934,041

(22) Filed: Oct. 31, 2024

(65) Prior Publication Data

US 2025/0171804 A1 May 29, 2025

Related U.S. Application Data

(62) Division of application No. 18/517,808, filed on Nov. 22, 2023, now Pat. No. 12,195,747.

(51) Int. Cl.

*C12N 15/86* (2006.01)
*C12N 15/11* (2006.01)
*C12N 15/113* (2010.01)

(52) U.S. Cl.

CPC .......... *C12N 15/1136* (2013.01); *C12N 15/86* (2013.01); *C12N 2310/141* (2013.01); *C12N 2750/14141* (2013.01)

(58) Field of Classification Search

CPC ................. C12N 15/86; C12N 15/111; C12N 2310/141; C12N 2750/14141

See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 | 11/2021 | Munshull et al. | |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1 | 11/2024 | Thompson | |
| 12,195,747 B1 | 1/2025 | Thompson | |
| 2024/0026377 A1 | 1/2024 | Thompson | |
| 2024/0366789 A1* | 11/2024 | Fu | A61P 3/00 |

FOREIGN PATENT DOCUMENTS

| | | |
|---|---|---|
| CA | 2721333 A1 | 10/2009 |
| CN | 108998451 A | 12/2018 |

OTHER PUBLICATIONS

O'Brien, et al. "Overview of MicroRNA Biogenesis, Mechanisms of Actions, and Circulation." Front Endocrinol (Lausanne), (2018) 9: 402, p. 1-12. (Year: 2018).*

Gorski, S., Vogel, J. & Doudna, J. "RNA-based recognition and targeting_ sowing the seeds of specificity". Nat Rev Mol Cell Biol 18 (2017), 215-228. (Year: 2017).*

Lam et al. "siRNA Versus miRNA as Therapeutics for Gene Silencing". Molecular Therapy. Nucleic Acids. vol. 4 (2015) pp. e252-e252. (Year: 2015).*

Ying et al."The MicroRNA (miRNA): Overview of the RNA Genes that Modulate Gene Function". Mol. Biotechnol. (2008) 38:257-268. (Year: 2008).*

Van den Berg, et al. "Design of Effective Primary MicroRNA Mimics With Different Basal Stem Conformations". Molecular Therapy—Nucleic Acids, vol. 5 (2016), pp. 1-12. (Year: 2016).*

Denzler R et al."Impact of MicroRNA Levels, Target-Site Complementarity, and Cooperativity on Competing Endogenous RNA-Regulated Gene Expression." Mol Cell. Nov. 3, 2016;64(3):565-579. (Year: 2016).*

Zhang et al. "Cytokines, inflammation, and pain." International anesthesiology clinics 45.2 (2007): 27-37.

WIPO translation of CN108998451 (2018).

Asirvatham et al. "miRNA regulation of cytokine genes." Cytokine 45.2 (2009): 58-69.

Christensen et al. "Recombinant adeno-associated virus-mediated microRNA delivery into the postnatal mouse brain reveals a role for miR-134 in dendritogenesis in vivo." Frontiers in neural circuits 3 (2010): 848.

Bofill-De Ros et al. "Guidelines for the optimal design of miRNA-based shRNAs." Methods 103 (2016): 157-166.

Tritschler et al. "Concepts and limitations for learning developmental trajectories from single cell genomics." Development 146.12 (2019): dev170506.

Nature (2010. Gene Expression. Scitable. Available online at Nature.com) <https://www.nature.com/scitable/topicpage/gene-expression-14121669> (2010).

Shang et al. "microRNAs in action: biogenesis, function and regulation." Nature Reviews Genetics 24.12 (2023): 816-833.

Agarwal et al. "Predicting effective microRNA target sites in mammalian mRNAs." elife 4 (2015): e05005.

Fayyad-Kazan et al. "Downregulation of microRNA-24 and-181 parallels the upregulation of IFN-γ secreted by activated human CD4 lymphocytes." Human immunology 75.7 (2014): 677-685.

Patton et al. "Biogenesis, delivery, and function of extracellular RNA." Journal of extracellular vesicles 4.1 (2015): 27494.

NCBI Search results for SEQ ID No. 5 2024.

(Continued)

*Primary Examiner* — Neil P Hammell
*Assistant Examiner* — Alexandra Geraldine Dace Denito
(74) *Attorney, Agent, or Firm* — Gowling WLG (Canada) LLP

(57) ABSTRACT

The embodiments of the present disclosure relate to decreasing the bioavailability of one or more target biomolecules by providing a composition that comprises a recombinant plasmid with one or more sequences of micro interfering ribonucleic acid (miRNA). When the recombinant plasmid interacts with a target cell, it causes the target cell to upregulate production of the miRNA, which then decreases the bioavailability of the target biomolecule. In some embodiments of the present disclosure, the target biomolecule is a cytokine or other mediator molecule of an inflammatory response.

3 Claims, No Drawings

Specification includes a Sequence Listing.

(56) References Cited

OTHER PUBLICATIONS

Depieri et al. "RNAi mediated IL-6 in vitro knockdown in psoriasis skin model with topical siRNA delivery system based on liquid crystalline phase." European Journal of Pharmaceutics and Biopharmaceutics 105 (2016): 50-58.
*Homo sapiens* interferon-gamma mRNA 2002.
Kondratov et al. "Direct head-to-head evaluation of recombinant adeno-associated viral vectors manufactured in human versus insect cells." Molecular Therapy 25.12 (2017): 2661-2675.
Wang et al. "Adeno-associated virus vector as a platform for gene therapy delivery". Nat Rev Drug Discov. May 2019;18(5):358-378. (Year: 2019).
Momin et al., 2021, Cells, 10, 3097, p. 1-21 (Year: 2021).
"The Risks of miRNA Therapeutics: In a Drug Target Perspective" (Zhang et al.—2021).
Li et al. "miR-190a-5p partially represses the abnormal electrical activity of SCN3B in cardiac arrhythmias by downregulation of IL-2." Frontiers in Cardiovascular Medicine 8 (2022): 795675.
Xu et al. "MicroRNA-26a-mediated regulation of interleukin-2 expression in transformed avian lymphocyte lines." Cancer cell international 10 (2010): 1-7.
Ahmadzadeh et al. "BRAF mutation in hairy cell leukemia." Oncology reviews 8.2 (2014): 253.

* cited by examiner

COMPOSITION FOR REGULATING PRODUCTION OF INTERFERING RIBONUCLEIC ACID

CROSS REFERENCE TO RELATED APPLICATION

The present application is a division of U.S. patent application Ser. No. 18/517,808 filed Nov. 22, 2023, entitled "Composition For Regulating Production Of Interfering Ribonucleic Acid" currently pending, the entirety of which is incorporated herein by reference.

SEQUENCE LISTING

This application contains a Sequence Listing electronically submitted via Patent Center to the United States Patent and Trademark Office as an XML Document file entitled "A8149360US—Sequence Listing.xml" created on 2023 Nov. 17 and having a size of 92,590 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and therefore, the production of interfering RNA that will suppress cytokine overexpression or mis-expression.

BACKGROUND

Bioactive molecules, including cytokines, are necessary for the homeostatic control of biological systems.

When bioactive molecules are over-expressed or mis-expressed, homeostasis is lost, and disease is often the result.

As such, it may be desirable to establish therapies, treatments and/or interventions that address when homeostasis and regulation of bioactive molecules is lost to prevent or treat a resulting disease.

SUMMARY

Some embodiments of the present disclosure relate to one or more compositions that upregulate the production of one or more sequences of micro interfering ribonucleic acid (miRNA). The sequences of miRNA may be complimentary to a sequence of target messenger RNA (mRNA) that encodes for translation of a target biomolecule and the miRNA can cause the bioavailability of the target mRNA to decrease because it is degraded or inactivated by the miRNA, thereby causing a decrease in bioavailability of the target biomolecule within a subject that is administered the one or more compositions. In some embodiments of the present disclosure, the target biomolecule is a cytokine. In some embodiments of the present disclosure, the target biomolecule is a cytokine such as IL-1beta. In some embodiments of the present disclosure, the target biomolecule is a cytokine such as IL-18. In some embodiments of the present disclosure, the target biomolecule is a cytokine such as IL-6. In some embodiments of the present disclosure, the target biomolecule is a cytokine such as IL-17A. In some embodiments of the present disclosure, the target biomolecule is a cytokine such as interferon gamma. In some embodiments of the present disclosure, the target biomolecule is a cytokine such as IL-2. In some embodiments of the present disclosure, the target biomolecule is a cytokine such as IL-4. In some embodiments of the present disclosure, the target biomolecule is a cytokine such as IL-5. In some embodiments of the present disclosure, the target biomolecule is a cytokine such as IL-10. In some embodiments of the present disclosure, the target biomolecule is a cytokine such as IL-22.

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells. In some embodiments of the present disclosure, the plasmid is a circular vector with a backbone sequence that comprises a start region, for example at the $3^1$ end of the sequence, and an end region, for example at a $5^1$ end of the sequence. The one or more insert sequences are inserted into the backbone sequence so as to connect the start region to the end region. For example, the one or more insert sequences may be inserted to connected at both the $3^1$ end of the backbone sequence and the $5^1$ end of the backbone sequence to connect the two ends of the backbone sequence so as to form the circular vector.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets mRNA of IL-1beta.

In some embodiments of the present disclosure, the RP comprises a nucleotide sequence of SEQ ID NO. 1 and SEQ ID NO. 3. In these embodiments, the RP comprises a nucleotide sequence encoding one or more nucleotide sequences encoding a miRNA sequence that targets mRNA of IL-18.

In some embodiments of the present disclosure, the RP comprises a nucleotide sequence of SEQ ID NO. 1 and SEQ ID NO. 4. In these embodiments, the RP comprises a nucleotide sequence encoding one or more nucleotide sequences encoding a miRNA sequence that targets mRNA of IL-6.

In some embodiments of the present disclosure, the RP comprises a nucleotide sequence of SEQ ID NO. 1 and SEQ ID NO. 5. In these embodiments, the RP comprises a nucleotide sequence encoding one or more nucleotide sequences encoding a miRNA sequence that targets mRNA of IL-17A.

In some embodiments of the present disclosure, the RP comprises a nucleotide sequence of SEQ ID NO. 1 and SEQ ID NO. 6. In these embodiments, the RP comprises a nucleotide sequence encoding one or more nucleotide sequences encoding a miRNA sequence that targets mRNA of interferon gamma.

In some embodiments of the present disclosure, the RP comprises a nucleotide sequence of SEQ ID NO. 1 and SEQ ID NO. 7. In these embodiments, the RP comprises a nucleotide sequence encoding one or more nucleotide sequences encoding a miRNA sequence that targets mRNA of IL-2.

In some embodiments of the present disclosure, the RP comprises a nucleotide sequence of SEQ ID NO. 1 and SEQ ID NO. 8. In these embodiments, the RP comprises a nucleotide sequence encoding one or more nucleotide sequences encoding a miRNA sequence that targets mRNA of IL-4.

In some embodiments of the present disclosure, the RP comprises a nucleotide sequence of SEQ ID NO. 1 and SEQ ID NO. 9. In these embodiments, the RP comprises a nucleotide sequence encoding one or more nucleotide sequences encoding a miRNA sequence that targets mRNA of IL-5.

In some embodiments of the present disclosure, the RP comprises a nucleotide sequence of SEQ ID NO. 1 and SEQ ID NO. 10. In these embodiments, the RP comprises a nucleotide sequence encoding one or more nucleotide sequences encoding a miRNA sequence that targets mRNA of IL-10.

In some embodiments of the present disclosure, the RP comprises a nucleotide sequence of SEQ ID NO. 1 and SEQ ID NO. 11. In these embodiments, the RP comprises a nucleotide sequence encoding one or more nucleotide sequences encoding a miRNA sequence that targets mRNA of IL-22.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, or SEQ ID NO. 11, to a target cell for forming the composition/target cell complex, wherein the composition/target cell complex causes the target cell to increase production of one or more sequences of miRNA that decreases production of a target biomolecule.

Some embodiments of the present disclosure relate to at least one approach for inducing endogenous production of one or more sequences of miRNA that target and silence mRNA of a target biomolecule, for example IL-1beta. A first approach utilizes gene vectors containing nucleotide sequences for increasing the endogenous production of one or more sequences of miRNA, which are complete or partial sequences and/or combinations thereof, that target and silence the mRNA of IL-1beta, which can be administered to a subject to increase the subject's production of one or more sequences of the miRNA.

Some embodiments of the present disclosure relate to at least one approach for inducing endogenous production of one or more sequences of miRNA that target and silence mRNA of a target biomolecule, for example IL-18. A first approach utilizes gene vectors containing nucleotide sequences for increasing the endogenous production of one or more sequences of miRNA, which are complete or partial sequences and/or combinations thereof, that target and silence the mRNA of IL-18, which can be administered to a subject to increase the subject's production of one or more sequences of the miRNA.

Some embodiments of the present disclosure relate to at least one approach for inducing endogenous production of one or more sequences of miRNA that target and silence mRNA of a target biomolecule, for example IL-6. A first approach utilizes gene vectors containing nucleotide sequences for increasing the endogenous production of one or more sequences of miRNA, which are complete or partial sequences and/or combinations thereof, that target and silence the mRNA of IL-6, which can be administered to a subject to increase the subject's production of one or more sequences of the miRNA.

Some embodiments of the present disclosure relate to at least one approach for inducing endogenous production of one or more sequences of miRNA that target and silence mRNA of a target biomolecule, for example IL-17A. A first approach utilizes gene vectors containing nucleotide sequences for increasing the endogenous production of one or more sequences of miRNA, which are complete or partial sequences and/or combinations thereof, that target and silence the mRNA of IL-17A, which can be administered to a subject to increase the subject's production of one or more sequences of the miRNA.

Some embodiments of the present disclosure relate to at least one approach for inducing endogenous production of one or more sequences of miRNA that target and silence mRNA of a target biomolecule, for example interferon gamma. A first approach utilizes gene vectors containing nucleotide sequences for increasing the endogenous production of one or more sequences of miRNA, which are complete or partial sequences and/or combinations thereof, that target and silence the mRNA of interferon gamma, which can be administered to a subject to increase the subject's production of one or more sequences of the miRNA.

Some embodiments of the present disclosure relate to at least one approach for inducing endogenous production of one or more sequences of miRNA that target and silence mRNA of a target biomolecule, for example IL-2. A first approach utilizes gene vectors containing nucleotide sequences for increasing the endogenous production of one or more sequences of miRNA, which are complete or partial sequences and/or combinations thereof, that target and silence the mRNA of IL-2, which can be administered to a subject to increase the subject's production of one or more sequences of the miRNA.

Some embodiments of the present disclosure relate to at least one approach for inducing endogenous production of one or more sequences of miRNA that target and silence mRNA of a target biomolecule, for example IL-4. A first approach utilizes gene vectors containing nucleotide sequences for increasing the endogenous production of one or more sequences of miRNA, which are complete or partial sequences and/or combinations thereof, that target and silence the mRNA of IL-4, which can be administered to a subject to increase the subject's production of one or more sequences of the miRNA.

Some embodiments of the present disclosure relate to at least one approach for inducing endogenous production of one or more sequences of miRNA that target and silence mRNA of a target biomolecule, for example IL-5. A first approach utilizes gene vectors containing nucleotide sequences for increasing the endogenous production of one or more sequences of miRNA, which are complete or partial sequences and/or combinations thereof, that target and silence the mRNA of IL-5, which can be administered to a subject to increase the subject's production of one or more sequences of the miRNA.

Some embodiments of the present disclosure relate to at least one approach for inducing endogenous production of one or more sequences of miRNA that target and silence mRNA of a target biomolecule, for example IL-10. A first approach utilizes gene vectors containing nucleotide sequences for increasing the endogenous production of one or more sequences of miRNA, which are complete or partial sequences and/or combinations thereof, that target and silence the mRNA of IL-10, which can be administered to a subject to increase the subject's production of one or more sequences of the miRNA.

Some embodiments of the present disclosure relate to at least one approach for inducing endogenous production of one or more sequences of miRNA that target and silence mRNA of a target biomolecule, for example IL-22. A first approach utilizes gene vectors containing nucleotide sequences for increasing the endogenous production of one or more sequences of miRNA, which are complete or partial sequences and/or combinations thereof, that target and silence the mRNA of IL-22, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "ameliorate" refers to improve and/or to make better and/or to make more satisfactory.

As used therein, the term "biomolecule" refers to a cytokine that is found within a subject. A biomolecule may be endogenous or exogenous to a subject.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is IL-1beta.

In some embodiments of the present disclosure, the target biomolecule is IL-18.

In some embodiments of the present disclosure, the target biomolecule is IL-6.

In some embodiments of the present disclosure, the target biomolecule is IL-17A.

In some embodiments of the present disclosure, the target biomolecule is interferon gamma.

In some embodiments of the present disclosure, the target biomolecule is IL-2.

In some embodiments of the present disclosure, the target biomolecule is IL-4.

In some embodiments of the present disclosure, the target biomolecule is IL-5.

In some embodiments of the present disclosure, the target biomolecule is IL-10.

In some embodiments of the present disclosure, the target biomolecule is IL-22.

In some embodiments of the present disclosure, the insert comprises one or more nucleotide sequences that each encode one or more miRNA sequences that may be complimentary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complimentary to and degrade, or cause degradation of, one biomolecule, such as IL-1beta, IL-18, IL-6, IL-17A, interferon gamma, IL-2, IL-4, IL-5, IL-10, or IL-22. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complimentary to and degrade, or cause degradation of, or inactivate, or cause inactivation of, one biomolecule, such as IL-1beta, IL-18, IL-6, IL-17A, interferon gamma, IL-2, IL-4, IL-5, IL-10, or IL-22. Increased endogenous expression of the one or more miRNA sequences results in a decreased bioavailability of the desired biomolecule, which may also be referred to as a target biomolecule.

In some embodiments of the present disclosure, the delivery vehicle of the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ $TCID_{50}$/kg (50% tissue culture infective dose per kilogram of the patient's body mass. In some embodiments of the present disclosure, the therapeutically effective amount of the composition that is administered to the patient is about $1\times10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1\times10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of a biomolecule, with examples being IL-1 beta, IL-18, IL-6, IL-17A, interferon gamma, IL-2, IL-4, IL-5, IL-10, or IL-22. The RP is comprised of AAV2 inverted terminal repeats (ITRs), a composite CASI promoter, a human growth hormone (HGH) signal peptide followed by a miRNA expression cassette containing up to six different miRNAs targeting IL-1 beta, IL-18, IL-6, IL-17A, interferon gamma, IL-2, IL-4, IL-5, IL-10, or IL-22, followed by a Woodchuck Hepatitis Virus post-transcriptional regulatory element (WPRE) and an SV40 polyA signal.

```
(backbone sequence No. 1):
                                                                  SEQ ID NO. 1
5'
aatcaacctctggattacaaaatttgtgaaagattgactggtattcttaactatgttgctccttttacgctatgtggatacgctgctttaatgcctttgt

atcatgctattgcttcccgtatggctttcattttctcctccttgtataaatcctggttgctgtctctttatgaggagttgtggcccgttgtcaggcaac

gtggcgtggtgtgcactgtgtttgctgacgcaacccccactggttggggcattgccaccacctgtcagctcctttccgggactttcgctttccc

cctccctattgccacggcggaactcatcgccgcctgccttgcccgctgctggacaggggctcggctgttgggcactgacaattccgtggtgt

tgtcggggaaatcatcgtcctttccttggctgctcgcctgtgttgccacctggattctgcgcgggacgtccttctgctacgtcccttcggccctc

aatccagcggaccttccttcccgcggcctgctgccggctctgcggcctcttccgcgtcttcgccttcgccctcagacgagtcggatctcccttt

gggccgcctccccgcctaagcttatcgataccgtcgagatctaacttgtttattgcagcttataatggttacaaataaagcaatagcatcacaaa

tttcacaaataaagcatttttttcactgcattctagttgtggtttgtccaaactcatcaatgtatcttatcatgtctggatctcgacctcgactagagc

atggctacgtagataagtagcatggcgggttaatcattaactacaaggaacccctagtgatggagttggccactccctctctgcgcgctcgct

cgctcactgaggccgggcgaccaaaggtcgcccgacgcccgggctttgcccgggcggcctcagtgagcgagcgagcgcgcagctgg

cgtaatagcgaagaggcccgcaccgatcgcccttcccaacagttgcgcagcctgaatggcgaatggcgattccgttgcaatggctggcgg

taatattgttctggatattaccagcaaggccgatagtttgagttcttctactcaggcaagtgatgttattactaatcaaagaagtattgcgacaac

ggttaatttgcgtgatggacagactcttttactcggtggcctcactgattataaaaacacttctcaggattctggcgtaccgttcctgtctaaaatc

cctttaatcggcctcctgtttagctcccgctctgattctaacgaggaaagcacgttatacgtgctcgtcaaagcaaccatagtacgcgccctgt

agcggcgcattaagcgcggcgggtgtggtggttacgcgcagcgtgaccgctacacttgccagcgccctagegcccgctcctttcgctttctt

cccttcctttctcgccacgttcgccggctttccccgtcaagctctaaatcgggggctccctttagggttccgatttagtgctttacggcacctcga

ccccaaaaaacttgattagggtgatggttcacgtagtgggccatcgccctgatagacggtttttcgccctttgacgttggagtccacgttcttta

atagtggactcttgttccaaactggaacaacactcaaccctatctcggtctattcttttgatttataagggattttgccgatttcggcctattggttaa

aaaatgagctgatttaacaaaaatttaacgcgaattttaacaaaatattaacgtttacaatttaaatatttgcttatacaatcttcctgtttttggggct

tttctgattatcaaccggggtacatatgattgacatgctagttttacgattaccgttcatcgattctcttgtttgctccagactctcaggcaatgacct

gatagcctttgtagagacctctcaaaaatagctaccctctccggcatgaatttatcagctagaacggttgaatatcatattgatggtgatttgact

gtctccggcctttctcacccgtttgaatctttacctacacattactcaggcattgcatttaaaatatatgagggttctaaaaatttttatccttgcgttg

aaataaaggcttctcccgcaaaagtattacagggtcataatgtttttggtacaaccgatttagctttatgctctgaggctttattgcttaattttgcta

attctttgccttgcctgtatgatttattggatgttggaattcctgatgcggtattttctccttacgcatctgtgcggtatttcacaccgcatatggtgca

ctctcagtacaatctgctctgatgccgcatagttaagccagccccgacacccgccaacacccgctgacgcgccctgacgggcttgtctgctc

ccggcatccgcttacagacaagctgtgaccgtctccgggagctgcatgtgtcagaggttttcaccgtcatcaccgaaacgcgcgagacgaa

agggcctcgtgatacgcctatttttataggttaatgtcatgataataatggtttcttagacgtcaggtggcacttttcggggaaatgtgcgcggaa

cccctatttgtttatttttctaaatacattcaaatatgtatccgctcatgagacaataaccctgataaatgcttcaataatattgaaaaaggaagagt

atgagtattcaacatttccgtgtcgcccttattcccttttttgcggcattttgccttcctgtttttgctcacccagaaacgctggtgaaagtaaaagat

gctgaagatcagttgggtgcacgagtgggttacatcgaactggatctcaacagcggtaagatccttgagagttttcgccccgaagaacgtttt

ccaatgatgagcacttttaaagttctgctatgtggcgcggtattatcccgtattgacgccgggcaagagcaactcggtcgccgcatacactatt

ctcagaatgacttggttgagtactcaccagtcacagaaaagcatcttacggatggcatgacagtaagagaattatgcagtgctgccataacca

tgagtgataacactgcggccaacttacttctgacaacgatcggaggaccgaaggagctaaccgctttttttgcacaacatgggggatcatgta

actcgccttgatcgttgggaaccggagctgaatgaagccataccaaacgacgagcgtgacaccacgatgcctgtagcaatggcaacaacg
```

-continued ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttctttttttttctacaggtcctgggtgacgaacagggtaccgccaccatggc caccggctctcgcacaagcctgctgctggctttcggactgctgtgcctgccttggctccaggagggctccgcc

3'

(miRNA expression cassette No. 2 - IL-1 beta):

SEQ ID NO. 2

5' gctagcatcgataccgtcgctatgtgctggaggcttgctgaaggctgtatgctggactatgactcgggaaatattgttttggcctctgactgac aatatttcccggtagtcatagtccaggacacaaggcctgttactagcactcacatggaacaaatggcctctagcctggaggcttgctgaagg ctgtatgctggcccacattctagtcttgagtgttttggcctctgactgacactcaagactaatgaatgtgggccaggacacaaggcctgttacta gcactcacatggaacaaatggcctctagcctggaggcttgctgaaggctgtatgctggaatcgggtagtaagagtgatgttttggcctctgac tgacatcactcttacaatacccgattccaggacacaaggcctgttactagcactcacatggaacaaatggcctctctagaat -continued

3'

(miRNA expression cassette No. 3 - IL-18):

SEQ ID NO. 3

5' gctagcatcgataccgtcgctatgtgctggaggcttgctgaaggctgtatgctgtgtttagtggctgtgaactcaccgttttggcctctgactga
cggtgagttcagccactaaacacaggacacaaggcctgttactagcactcacatggaacaaatggcctctagcctggaggcttgctgaagg
ctgtatgctgatctttcatccatcgtaactcccgttttggcctctgactgacgggagttacgggatgaaagatcaggacacaaggcctgttacta
gcactcacatggaacaaatggcctctagcctggaggcttgctgaaggctgtatgctgacatgaatgagaaagttggctccgttttggcctctg
actgacggagccaactctcattcatgtcaggacacaaggcctgttactagcactcacatggaacaaatggcctctctagaat

3'

(miRNA expression cassette No. 4 - IL - 6):

SEQ ID NO. 4

5' gctagcatcgataccgtcgctatgtgctggaggcttgctgaaggctgtatgctgagtgatatgcgtgcagaacagtcgttttggcctctgactg
acgactgttctgcgcatatcactcaggacacaaggcctgttactagcactcacatggaacaaatggcctctagcctggaggcttgctgaagg
ctgtatgctgactcaagactaatgaatgtgggcgttttggcctctgactgacgcccacattctagtcttgagtcaggacacaaggcctgttacta
gcactcacatggaacaaatggcctctagcctggaggcttgctgaaggctgtatgctgtctattactgcaatcactgtggcgttttggcctctga
ctgacgccacagtgagcagtaatagacaggacacaaggcctgttactagcactcacatggaacaaatggcctctctagaat

3'

(miRNA expression cassette No. 5 - IL-17A):

SEQ ID NO. 5

5' gctagcatcgataccgtcgctatgtgctggaggcttgctgaaggctgtatgctgaggatagggattgtattggaggcgttttggcctctgactg
acgcctccaataatccctatcctcaggacacaaggcctgttactagcactcacatggaacaaatggcctctagcctggaggcttgctgaagg
ctgtatgctgtatgaccttctatcttccctctcgttttggcctctgactgacgagagggaagagaaggtcatacaggacacaaggcctgttacta
gcactcacatggaacaaatggcctctagcctggaggcttgctgaaggctgtatgctgttagtccgaaaaatgaggctgtcgttttggcctctg
actgacgacagcctcatttcggactaacaggacacaaggcctgttactagcactcacatggaacaaatggcctctctagaat

3'

(miRNA expression cassette No. 6 - interferon gamma):

SEQ ID NO. 6

5' gctagcatcgataccgtcgctatgtgctggaggcttgctgaaggctgtatgctgatgacagcctatgtcagagatgcgttttggcctctgactg
acgcatctctgataggctgtcatcaggacacaaggcctgttactagcactcacatggaacaaatggcctctagcctggaggcttgctgaagg
ctgtatgctgactacttgcatatctcctcactcgttttggcctctgactgacgagtgaggagatgcaagtagtcaggacacaaggcctgttacta
gcactcacatggaacaaatggcctctagcctggaggcttgctgaaggctgtatgctgactgatctaggaattaggtacccgttttggcctctg
actgacgggtacctaacctagatcagtcaggacacaaggcctgttactagcactcacatggaacaaatggcctctctagaat

3'

(miRNA expression cassette No. 7 - IL-2):

SEQ ID NO. 7

5' gctagcatcgataccgtcgctatgtgctggaggcttgctgaaggctgtatgctgtgctattagtctgccatctgtgcgttttggcctctgactga
cgcacagatgggactaatagcacaggacacaaggcctgttactagcactcacatggaacaaatggcctctagcctggaggcttgctgaag
gctgtatgctgtgtgaaactcaatactcagtaccgttttggcctctgactgacggtactgagttgagtttcacacaggacacaaggcctgttact
agcactcacatggaacaaatggcctctagcctggaggcttgctgaaggctgtatgctgtacatcacctgaaagtcccttgcgttttggcctctg
actgacgcaagggactcaggtgatgtacaggacacaaggcctgttactagcactcacatggaacaaatggcctctctagaat -continued

3'

(miRNA expression cassette No. 8 - IL-4):

SEQ ID NO. 8

5' gctagcatcgataccgtcgctatgtgctggaggcttgctgaaggctgtatgctgaagatgtctgttgtacggtcaacgttttggcctctgactga cgttgaccgtaacagacatcttcaggacacaaggcctgttactagcactcacatggaacaaatggcctctagcctggaggcttgctgaaggc tgtatgctgactaactcaagatagctggattcgttttggcctctgactgacgaatccagctcttgagttagtcaggacacaaggcctgttactag cactcacatggaacaaatggcctctagcctggaggcttgctgaaggctgtatgctgtagaatgcaggaaaccatctgtcgttttggcctctga ctgacgacagatggtcctgcattctacaggacacaaggcctgttactagcactcacatggaacaaatggcctctctagaata

3'

(miRNA expression cassette No. 9 - IL-5):

SEQ ID NO. 9

5' gctagcatcgataccgtcgctatgtgctggaggcttgctgaaggctgtatgctgtactgttcgacctgtcacatcatcgttttggcctctgactg acgatgatgtgaggtcgaacagtcaggacacaaggcctgttactagcactcacatggaacaaatggcctctagcctggaggcttgctgaag gctgtatgctgtctgttgacgtatcgtgatctgcgttttggcctctgactgacgcagatcacgacgtcaacagacaggacacaaggcctgttac tagcactcacatggaacaaatggcctctagcctggaggcttgctgaaggctgtatgctgtgagtgtaatgaacagttggcacgttttggcctct gactgacgtgccaactgcattacactcacaggacacaaggcctgttactagcactcacatggaacaaatggcctctctagaat

3'

(miRNA expression cassette No. 10 - IL-10):

SEQ ID NO. 10

5' gctagcatcgataccgtcgctatgtgctggaggcttgctgaaggctgtatgctgtaaatttcccttggctgcaaggcgttttggcctctgactga cgccttgcagcagggaaatttacaggacacaaggcctgttactagcactcacatggaacaaatggcctctagcctggaggcttgctgaagg ctgtatgctgagtttagcttgatgaaagatcccgttttggcctctgactgacgggatctttccaagctaaactcaggacacaaggcctgttacta gcactcacatggaacaaatggcctctagcctggaggcttgctgaaggctgtatgctgacttaaatcagaagtcctcctccgttttggcctctga ctgacggaggaggacctgatttaagtcaggacacaaggcctgttactagcactcacatggaacaaatggcctctctagaat

3'

(miRNA expression cassette No. 11- IL-22):

SEQ ID NO. 11

5' gctagcatcgataccgtcgctatgtgctggaggcttgctgaaggctgtatgctgggtgaaggaggatcgcctagaagttttggcctctgactg actaaaatttccctgtgctgcaaggacaggacacaaggcctgttactagcactcacatggaacaaatggcctctagcctggaggcttgctga aggctgtatgctgggaggaggacctgatttaagtgttttggcctctgactgacacttaaatcagatgtcctcctcccaggacacaaggcctgtt actagcactcacatggaacaaatggcctctagcctggaggcttgctgaaggctgtatgctgggtgaaggaggatcgctagaagttttggcct ctgactgacttctagcgatcaactccttcacccaggacacaaggcctgttactagcactcacatggaacaaatggcctctctagaat

3'

As will be appreciated by those skilled in the art, when one or more of the SEQ ID NO. 2-11 for the miRNA expression cassettes are inserted into the backbone sequence SEQ ID NO. 1, the resultant vector is circular with one or more miRNA expression cassettes inserted between the 5' and 3' ends of the backbone sequence (SEQ ID NO. 1). Accordingly, the following sequences represent further sequence listings that form part of this disclosure and that comprise SEQ ID NO. 1 with at least one of the SEQ ID NO. 2-11 inserted:

SEQ ID NO: 12 = SEQ ID NO. 1 + SEQ ID NO. 2:
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctccctttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct -continued tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctggactatgactcgggaaatattgttttggcctctgactgacaatatttcccggtagtcata gtccaggacacaaggcctgttactagcactcacatggaacaaatggcctctagcctggaggcttgctgaaggctgtatgctggcccacattc tagtcttgagtgttttggcctctgactgacactcaagactaatgaatgtgggccaggacacaaggcctgttactagcactcacatggaacaaat ggcctctagcctggaggcttgctgaaggctgtatgctggaatcgggtagtaagagtgatgttttggcctctgactgacatcactcttacaatac ccgattccaggacacaaggcctgttactagcactcacatggaacaaatggcctctctagaat

3'

SEQ ID NO: 13 = SEQ ID NO. 1 + SEQ ID NO. 3:
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct -continued cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct -continued aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtgtttagtggctgtgaactcaccgttttggcctctgactgacggtgagttcagccacta aacacaggacacaaggcctgttactagcactcacatggaacaaatggcctctagcctggaggcttgctgaaggctgtatgctgatctttcatc catcgtaactcccgttttggcctctgactgacgggagttacgggatgaaagatcaggacacaaggcctgttactagcactcacatggaacaa atggcctctagcctggaggcttgctgaaggctgtatgctgacatgaatgagaaagttggctccgttttggcctctgactgacggagccaactc tcattcatgtcaggacacaaggcctgttactagcactcacatggaacaaatggcctctctagaat

3'

SEQ ID NO: 14 = SEQ ID NO. 1 + SEQ ID NO. 4:
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggatttttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct -continued gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt cctttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt -continued gactctagggcactggttttctttccagagagcggaacaggcgaggaaaagtagtcccttctcggcgattctgcggagggatctccgtggg gcggtgaacgccgatgatgcctctactaaccatgttcatgttttcttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgagtgatatgcgtgcagaacagtcgttttggcctctgactgacgactgttctgcgcata tcactcaggacacaaggcctgttactagcactcacatggaacaaatggcctctagcctggaggcttgctgaaggctgtatgctgactcaaga ctaatgaatgtgggcgttttggcctctgactgacgcccacattctagtcttgagtcaggacacaaggcctgttactagcactcacatggaacaa atggcctctagcctggaggcttgctgaaggctgtatgctgtctattactgcaatcactgtggcgttttggcctctgactgacgccacagtgagc agtaatagacaggacacaaggcctgttactagcactcacatggaacaaatggcctctctagaat

3'

SEQ ID NO: 15 = SEQ ID NO. 1 + SEQ ID NO. 5:
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt -continued ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgaggatagggattgtattggaggcgttttggcctctgactgacgcctccaataatccct atcctcaggacacaaggcctgttactagcactcacatggaacaaatggcctctagcctggaggcttgctgaaggctgtatgctgtatgacctt ctatcttccctctcgttttggcctctgactgacgagagggaagagaaggtcatacaggacacaaggcctgttactagcactcacatggaaca aatggcctctagcctggaggcttgctgaaggctgtatgctgttagtccgaaaaatgaggctgtcgttttggcctctgactgacgacagcctcat ttcggactaacaggacacaaggcctgttactagcactcacatggaacaaatggcctctctagaat -continued

3'

SEQ ID NO: 16 = SEQ ID NO. 1 + SEQ ID NO. 6:
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttt ggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcattttttaatttaaaaggatctaggtg -continued aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgatgacagcctatgtcagagatgcgttttggcctctgactgacgcatctctgataggct gtcatcaggacacaaggcctgttactagcactcacatggaacaaatggcctctagcctggaggcttgctgaaggctgtatgctgactacttgc atatctcctcactcgttttggcctctgactgacgagtgaggagatgcaagtagtcaggacacaaggcctgttactagcactcacatggaacaa atggcctctagcctggaggcttgctgaaggctgtatgctgactgatctaggaattaggtacccgttttggcctctgactgacgggtacctaacc tagatcagtcaggacacaaggcctgttactagcactcacatggaacaaatggcctctctagaat

3'

SEQ ID NO: 17 = SEQ ID NO. 1 + SEQ ID NO. 7:
5'
aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc -continued atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga -continued gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtgctattagtctgccatctgtgcgttttggcctctgactgacgcacagatgggactaat agcacaggacacaaggcctgttactagcactcacatggaacaaatggcctctagcctggaggcttgctgaaggctgtatgctgtgtgaaact caatactcagtaccgttttggcctctgactgacggtactgagttgagtttcacacaggacacaaggcctgttactagcactcacatggaacaa atggcctctagcctggaggcttgctgaaggctgtatgctgtacatcacctgaaagtcccttgcgttttggcctctgactgacgcaagggactc aggtgatgtacaggacacaaggcctgttactagcactcacatggaacaaatggcctctctagaat

3'

SEQ ID NO: 18 = SEQ ID NO. 1 + SEQ ID NO. 8:
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggatttgccgatttcggcctattggttaa aaaatgagctgatttaacaaaaatttaacgcgaattttaacaaaatattaacgtttacaatttaaatatttgcttatacaatcttcctgtttttggggct -continued tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgccccccctcctcacggcgagcgctgccacgtcagacgaagggcgcagcgagcgtcctgatccttccgcc -continued cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgaagatgtctgttgtacggtcaacgttttggcctctgactgacgttgaccgtaacagac atcttcaggacacaaggcctgttactagcactcacatggaacaaatggcctctagcctggaggcttgctgaaggctgtatgctgactaactca agatagctggattcgttttggcctctgactgacgaatccagctcttgagttagtcaggacacaaggcctgttactagcactcacatggaacaaa tggcctctagcctggaggcttgctgaaggctgtatgctgtagaatgcaggaaaccatctgtcgttttggcctctgactgacgacagatggtcct gcattctacaggacacaaggcctgttactagcactcacatggaacaaatggcctctctagaata 3'

SEQ ID NO: 19 = SEQ ID NO. 1 + SEQ ID NO. 9:
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt -continued ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagcc gtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccggggcgccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtactgttcgacctgtcacatcatcgttttggcctctgactgacgatgatgtgaggtcga acagtcaggacacaaggcctgttactagcactcacatggaacaaatggcctctagcctggaggcttgctgaaggctgtatgctgtctgttga cgtatcgtgatctgcgttttggcctctgactgacgcagatcacgacgtcaacagacaggacacaaggcctgttactagcactcacatggaac aaatggcctctagcctggaggcttgctgaaggctgtatgctgtgagtgtaatgaacagttggcacgttttggcctctgactgacgtgccaact gcattacactcacaggacacaaggcctgttactagcactcacatggaacaaatggcctctctagaat -continued

3'

SEQ ID NO: 20 = SEQ ID NO. 1 + SEQ ID NO. 10:
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg -continued aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtaaatttcccttggctgcaaggcgttttggcctctgactgacgccttgcagcagggaa atttacaggacacaaggcctgttactagcactcacatggaacaaatggcctctagcctggaggcttgctgaaggctgtatgctgagtttagctt gatgaaagatcccgttttggcctctgactgacgggatctttccaagctaaactcaggacacaaggcctgttactagcactcacatggaacaaa tggcctctagcctggaggcttgctgaaggctgtatgctgacttaaatcagaagtcctcctccgttttggcctctgactgacggaggaggacct gatttaagtcaggacacaaggcctgttactagcactcacatggaacaaatggcctctctagaat

3'

SEQ ID NO: 21 = SEQ ID NO. 1 + SEQ ID NO. 11:
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc -continued atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca -continued

```
gctgcgcgctcgctcgctcactgaggccgcccgggcaaagcccgggcgtcgggcgacctttggtcgcccggcctcagtgagcgagcga

gcgcgcagagagggagtggccaactccatcactaggggttccttgtagttaatgattaacccgccatgctacttatctacgtagccatgctct

aggacattgattattgactagtggagttccgcgttacataacttacggtaaatggcccgcctggctgaccgcccaacgacccccgcccattg

acgtcaataatgacgtatgttcccatagtaacgccaatagggactttccattgacgtcaatgggtggagtatttacggtaaactgcccacttgg

cagtacatcaagtgtatcatatgccaagtacgccccctattgacgtcaatgacggtaaatggcccgcctggcattatgcccagtacatgacctt

atgggactttcctacttggcagtacatctacgtattagtcatcgctattaccatggtcgaggtgagccccacgttctgcttcactctccccatctc

ccccccctccccacccccaattttgtatttatttattttttaattattttgtgcagcgatgggggcgggggggggggggggcgcgcgccaggc

ggggcggggcggggcgaggggcggggcggggcgaggcggagaggtgcggcggcagccaatcagagcggcgcgctccgaaagttt

ccttttatggcgaggcggcggcggcggcggccctataaaaagcgaagcgcgcggcgggcgggagtcgctgcgcgctgccttcgcccc

gtgccccgctccgccgccgcctcgcgccgcccgccccggctctgactgaccgcgttactaaaacaggtaagtccggcctccgcgccggg

ttttggcgcctcccgcgggcgcccccctcctcacggcgagcgctgccacgtcagacgaagggcgcagcgagcgtcctgatccttccgcc

cggacgctcaggacagcggcccgctgctcataagactcggccttagaaccccagtatcagcagaaggacattttaggacgggacttgggt

gactctagggcactggttttctttccagagagcggaacaggcgaggaaaagtagtcccttctcggcgattctgcggagggatctccgtggg

gcggtgaacgccgatgatgcctctactaaccatgttcatgttttcttttttttctacaggtcctgggtgacgaacagggtaccgccaccatggc

caccggctctcgcacaagcctgctgctggctttcggactgctgtgcctgccttggctccaggagggctccgccgctagcatgataccgtc

gctatgtgctggaggcttgctgaaggctgtatgctgggtgaaggaggatcgcctagaagttttggcctctgactgactaaaatttccctgtgct

gcaaggacaggacacaaggcctgttactagcactcacatggaacaaatggcctctagcctggaggcttgctgaaggctgtatgctgggag

gaggacctgatttaagtgttttggcctctgactgacacttaaatcagatgtcctcctcccaggacacaaggcctgttactagcactcacatgga

acaaatggcctctagcctggaggcttgctgaaggctgtatgctgggtgaaggaggatcgctagaagttttggcctctgactgacttctagcga

tcaactccttcacccaggacacaaggcctgttactagcactcacatggaacaaatggcctctctagaat

3'
```

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 12-21 or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR. CASI promoter. miRNA expression cassette. WPRE. SV40 poly A and ITR 3'.

The invention claimed is:

1. A composition that comprises a recombinant plasmid (RP) comprising a sequence of nucleotides that is 100% identical to SEQ ID NO: 11.

2. The composition of claim 1, wherein the RP is encased in a protein coat, a lipid vesicle, or any combination thereof.

3. A composition that comprises a recombinant plasmid (RP) comprising a sequence of nucleotides that is 100% identical to SEQ ID NO: 21.

* * * * *

SEQUENCE LISTING

```
Sequence total quantity: 21
SEQ ID NO: 1            moltype = DNA  length = 5883
FEATURE                 Location/Qualifiers
source                  1..5883
                        mol_type = other DNA
                        organism = synthetic construct
SEQUENCE: 1
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
```

```
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gcc                                                                5883
```

```
SEQ ID NO: 2            moltype = DNA  length = 456
FEATURE                 Location/Qualifiers
source                  1..456
                        mol_type = other DNA
                        organism = synthetic construct
SEQUENCE: 2
gctagcatcg ataccgtcgc tatgtgctgg aggcttgctg aaggctgtat gctggactat  60
gactcgggaa atattgtttt ggcctctgac tgacaatatt tcccggtagt catagtccag  120
gacacaaggc ctgttactag cactcacatg gaacaaatgg cctctagcct ggaggcttgc  180
tgaaggctgt atgctggccc acattctagt cttgagtgtt ttggcctctg actgacactc  240
aagactaatg aatgtgggcc aggacacaag gcctgttact agcactcaca tggaacaaat  300
ggcctctagc ctggaggctt gctgaaggct gtatgctgga atcgggtagt aagagtgatg  360
ttttggcctc tgactgacat cactcttaca atacccgatt ccaggacaca aggcctgtta  420
ctagcactca catggaacaa atggcctctc tagaat                            456
```

```
SEQ ID NO: 3            moltype = DNA  length = 456
FEATURE                 Location/Qualifiers
source                  1..456
                        mol_type = other DNA
                        organism = synthetic construct
SEQUENCE: 3
gctagcatcg ataccgtcgc tatgtgctgg aggcttgctg aaggctgtat gctgtgttta  60
gtggctgtga actcaccgtt ttggcctctg actgacggtg agttcagcca ctaaacacag  120
gacacaaggc ctgttactag cactcacatg gaacaaatgg cctctagcct ggaggcttgc  180
tgaaggctgt atgctgatct ttcatcccatc gtaactcccg ttttggcctc tgactgacgg  240
gagttacggg atgaaagatc aggacacaag gcctgttact agcactcaca tggaacaaat  300
ggcctctagc ctggaggctt gctgaaggct gtatgctgac atgaatgaga aagttggctc  360
cgttttggcc tctgactgac ggagccaact ctcattcatg tcaggacaca aggcctgtta  420
ctagcactca catggaacaa atggcctctc tagaat                            456
```

```
SEQ ID NO: 4            moltype = DNA  length = 456
FEATURE                 Location/Qualifiers
source                  1..456
                        mol_type = other DNA
                        organism = synthetic construct
SEQUENCE: 4
gctagcatcg ataccgtcgc tatgtgctgg aggcttgctg aaggctgtat gctgagtgat  60
atgcgtgcag aacagtcgtt ttggcctctg actgacgact gttctgcgca tatcactcag  120
gacacaaggc ctgttactag cactcacatg gaacaaatgg cctctagcct ggaggcttgc  180
tgaaggctgt atgctgactc aagactaatg aatgtgggcg ttttggcctc tgactgacgc  240
ccacattcta gtcttgagtc aggacacaag gcctgttact agcactcaca tggaacaaat  300
ggcctctagc ctggaggctt gctgaaggct gtatgctgtc tattactgca atcactgtgg  360
cgttttggcc tctgactgac gccacagtga gcagtaatag acaggacaca aggcctgtta  420
ctagcactca catggaacaa atggcctctc tagaat                            456
```

```
SEQ ID NO: 5            moltype = DNA  length = 456
FEATURE                 Location/Qualifiers
source                  1..456
                        mol_type = other DNA
                        organism = synthetic construct
```

```
SEQUENCE: 5
gctagcatcg ataccgtcgc tatgtgctgg aggcttgctg aaggctgtat gctgaggata  60
gggattgtat tggaggcgtt ttggcctctg actgacgcct ccaataatcc ctatcctcag  120
gacacaaggc ctgttactag cactcacatg gaacaaatgg cctctagcct ggaggcttgc  180
tgaaggctgt atgctgtatg accttctatc ttccctctcg ttttggcctc tgactgacga  240
gagggaagag aaggtcatac aggacacaag gcctgttact agcactcaca tggaacaaat  300
ggcctctagc ctggaggctt gctgaaggct gtatgctgtt agtccgaaaa atgaggctgt  360
cgttttggcc tctgactgac gacagcctca tttcggacta acaggacaca aggcctgtta  420
ctagcactca catggaacaa atggcctctc tagaat                            456

SEQ ID NO: 6            moltype = DNA  length = 456
FEATURE                 Location/Qualifiers
source                  1..456
                        mol_type = other DNA
                        organism = synthetic construct
SEQUENCE: 6
gctagcatcg ataccgtcgc tatgtgctgg aggcttgctg aaggctgtat gctgatgaca  60
gcctatgtca gagatgcgtt ttggcctctg actgacgcat ctctgatagg ctgtcatcag  120
gacacaaggc ctgttactag cactcacatg gaacaaatgg cctctagcct ggaggcttgc  180
tgaaggctgt atgctgacta cttgcatatc tcctcactcg ttttggcctc tgactgacga  240
gtgaggagat gcaagtagtc aggacacaag gcctgttact agcactcaca tggaacaaat  300
ggcctctagc ctggaggctt gctgaaggct gtatgctgac tgatctagga attaggtacc  360
cgttttggcc tctgactgac gggtacctaa cctagatcag tcaggacaca aggcctgtta  420
ctagcactca catggaacaa atggcctctc tagaat                            456

SEQ ID NO: 7            moltype = DNA  length = 456
FEATURE                 Location/Qualifiers
source                  1..456
                        mol_type = other DNA
                        organism = synthetic construct
SEQUENCE: 7
gctagcatcg ataccgtcgc tatgtgctgg aggcttgctg aaggctgtat gctgtgctat  60
tagtctgcca tctgtgcgtt ttggcctctg actgacgcac agatgggact aatagcacag  120
gacacaaggc ctgttactag cactcacatg gaacaaatgg cctctagcct ggaggcttgc  180
tgaaggctgt atgctgtgtg aaactcaata ctcagtaccg ttttggcctc tgactgacgg  240
tactgagttg agtttcacac aggacacaag gcctgttact agcactcaca tggaacaaat  300
ggcctctagc ctggaggctt gctgaaggct gtatgctgta catcacctga aagtcccttg  360
cgttttggcc tctgactgac gcaagggact caggtgatgt acaggacaca aggcctgtta  420
ctagcactca catggaacaa atggcctctc tagaat                            456

SEQ ID NO: 8            moltype = DNA  length = 457
FEATURE                 Location/Qualifiers
source                  1..457
                        mol_type = other DNA
                        organism = synthetic construct
SEQUENCE: 8
gctagcatcg ataccgtcgc tatgtgctgg aggcttgctg aaggctgtat gctgaagatg  60
tctgttgtac ggtcaacgtt ttggcctctg actgacgttg accgtaacag acatcttcag  120
gacacaaggc ctgttactag cactcacatg gaacaaatgg cctctagcct ggaggcttgc  180
tgaaggctgt atgctgacta actcaagata gctggattcg ttttggcctc tgactgacga  240
atccagctct tgagttagtc aggacacaag gcctgttact agcactcaca tggaacaaat  300
ggcctctagc ctggaggctt gctgaaggct gtatgctgta gaatgcagga aaccatctgt  360
cgttttggcc tctgactgac gacagatggt cctgcattct acaggacaca aggcctgtta  420
ctagcactca catggaacaa atggcctctc tagaata                           457

SEQ ID NO: 9            moltype = DNA  length = 457
FEATURE                 Location/Qualifiers
source                  1..457
                        mol_type = other DNA
                        organism = synthetic construct
SEQUENCE: 9
gctagcatcg ataccgtcgc tatgtgctgg aggcttgctg aaggctgtat gctgtactgt  60
tcgacctgtc acatcatcgt tttggcctct gactgacgat gatgtgaggt cgaacagtca  120
ggacacaagg cctgttacta gcactcacat ggaacaaatg gcctctagcc tggaggcttg  180
ctgaaggctg tatgctgtct gttgacgtat cgtgatctgc gttttggcct ctgactgacg  240
cagatcacga cgtcaacaga caggacacaa ggcctgttac tagcactcac atggaacaaa  300
tggcctctag cctggaggct tgctgaaggc tgtatgctgt gagtgtaatg aacagttggc  360
acgttttggc ctctgactga cgtgccaact gcattacact cacaggacac aaggcctgtt  420
actagcactc acatggaaca aatggcctct ctagaat                           457

SEQ ID NO: 10           moltype = DNA  length = 456
FEATURE                 Location/Qualifiers
source                  1..456
                        mol_type = other DNA
                        organism = synthetic construct
SEQUENCE: 10
gctagcatcg ataccgtcgc tatgtgctgg aggcttgctg aaggctgtat gctgtaaatt  60
tcccttggct gcaaggcgtt ttggcctctg actgacgcct tgcagcaggg aaatttacag  120
gacacaaggc ctgttactag cactcacatg gaacaaatgg cctctagcct ggaggcttgc  180
```

```
tgaaggctgt atgctgagtt tagcttgatg aaagatcccg ttttggcctc tgactgacgg  240
gatctttcca agctaaactc aggacacaag gcctgttact agcactcaca tggaacaaat  300
ggcctctagc ctggaggctt gctgaaggct gtatgctgac ttaaatcaga agtcctcctc  360
cgttttggcc tctgactgac ggaggaggac ctgatttaag tcaggacaca aggcctgtta  420
ctagcactca catggaacaa atggcctctc tagaat                            456

SEQ ID NO: 11          moltype = DNA  length = 458
FEATURE                Location/Qualifiers
source                 1..458
                       mol_type = other DNA
                       organism = synthetic construct
SEQUENCE: 11
gctagcatcg ataccgtcgc tatgtgctgg aggcttgctg aaggctgtat gctgggtgaa  60
ggaggatcgc ctagaagttt tggcctctga ctgactaaaa tttccctgtg ctgcaaggac  120
aggacacaag gcctgttact agcactcaca tggaacaaat ggcctctagc ctggaggctt  180
gctgaaggct gtatgctggg aggaggacct gatttaagtg ttttggcctc tgactgacac  240
ttaaatcaga tgtcctcctc ccaggacaca aggcctgtta ctagcactca catggaacaa  300
atggcctcta gcctggaggc ttgctgaagg ctgtatgctg ggtgaaggag gatcgctaga  360
agttttggcc tctgactgac ttctagcgat caactccttc acccaggaca caaggcctgt  420
tactagcact cacatggaac aaatggcctc tctagaat                          458

SEQ ID NO: 12          moltype = DNA  length = 6339
FEATURE                Location/Qualifiers
source                 1..6339
                       mol_type = other DNA
                       organism = synthetic construct
SEQUENCE: 12
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
```

-continued tttttgcac aacatggggg atcatgtaac tcgccttgat cgttgggaac cggagctgaa 3180
tgaagccata ccaaacgacg agcgtgacac cacgatgcct gtagcaatgg caacaacgtt 3240
gcgcaaacta ttaactggcg aactacttac tctagcttcc cggcaacaat taatagactg 3300
gatggaggcg gataaagttg caggaccact tctgcgctcg gcccttccgg ctggctggtt 3360
tattgctgat aaatctggag ccggtgagcg tgggtctcgc ggtatcattg cagcactggg 3420
gccagatggt aagccctccc gtatcgtagt tatctacacg acggggagtc aggcaactat 3480
ggatgaacga aatagacaga tcgctgagat aggtgcctca ctgattaagc attggtaact 3540
gtcagaccaa gtttactcat atatacttta gattgattta aaacttcatt tttaatttaa 3600
aaggatctag gtgaagatcc tttttgataa tctcatgacc aaaatccctt aacgtgagtt 3660
ttcgttccac tgagcgtcag accccgtaga aaagatcaaa ggatcttctt gagatccttt 3720
ttttctgcgc gtaatctgct gcttgcaaac aaaaaaacca ccgctaccag cggtggtttg 3780
tttgccggat caagagctac caactctttt tccgaaggta actggcttca gcagagcgca 3840
gataccaaat actgtccttc tagtgtagcc gtagttaggc caccacttca agaactctgt 3900
agcaccgcct acatacctcg ctctgctaat cctgttacca gtggctgctg ccagtggcga 3960
taagtcgtgt cttaccgggt tggactcaag acgatagtta ccggataagg cgcagcggtc 4020
gggctgaacg gggggttcgt gcacacagcc cagcttggag cgaacgacct acaccgaact 4080
gagataccta cagcgtgagc tatgagaaag cgccacgctt cccgaaggga gaaaggcgga 4140
caggtatccg gtaagcggca gggtcggaac aggagagcgc acgagggagc ttccaggggg 4200
aaacgcctgg tatctttata gtcctgtcgg gtttcgccac ctctgacttg agcgtcgatt 4260
tttgtgatgc tcgtcagggg ggcggagcct atggaaaaac gccagcaacg cggccttttt 4320
acggttcctg gccttttgct ggccttttgc tcacatgttc tttcctgcgt tatcccctga 4380
ttctgtggat aaccgtatta ccgcctttga gtgagctgat accgctcgcc gcagccgaac 4440
gaccgagcgc agcgagtcag tgagcgagga agcggaagag cgcccaatac gcaaaccgcc 4500
tctccccgcg cgttggccga ttcattaatg cagcagctgc gcgctcgctc gctcactgag 4560
gccgcccggg caaagcccgg gcgtcgggcg acctttggtc gcccggcctc agtgagcgag 4620
cgagcgcgca gagagggagt ggccaactcc atcactaggg gttccttgta gttaatgatt 4680
aacccgccat gctacttatc tacgtagcca tgctctagga cattgattat tgactagtgg 4740
agttccgcgt tacataactt acggtaaatg gcccgcctgg ctgaccgccc aacgaccccc 4800
gcccattgac gtcaataatg acgtatgttc ccatagtaac gccaataggg actttccatt 4860
gacgtcaatg ggtggagtat ttacggtaaa ctgcccactt ggcagtacat caagtgtatc 4920
atatgccaag tacgccccct attgacgtca atgacggtaa atggcccgcc tggcattatg 4980
cccagtacat gaccttatgg gactttccta cttggcagta catctacgta ttagtcatcg 5040
ctattaccat ggtcgaggtg agccccacgt tctgcttcac tctccccatc tcccccccct 5100
ccccaccccc aattttgtat ttatttattt tttaattatt ttgtgcagcg atgggggcgg 5160
gggggggggg gggcgcgcgc caggcggggc ggggcggggc gaggggcggg gcggggcgag 5220
gcggagaggt gcggcggcag ccaatcagag cggcgcgctc cgaaagtttc cttttatggc 5280
gaggcggcgg cggcggcggc cctataaaaa gcgaagcgcg cggcgggcgg gagtcgctgc 5340
gcgctgcctt cgccccgtgc cccgctccgc cgccgcctcg cgccgcccgc cccggctctg 5400
actgaccgcg ttactaaaac aggtaagtcc ggcctccgcg ccgggttttg gcgcctcccg 5460
cgggcgcccc cctcctcacg gcgagcgctg ccacgtcaga cgaagggcgc agcgagcgtc 5520
ctgatccttc cgcccggacg ctcaggacag cggcccgctg ctcataagac tcggccttag 5580
aaccccagta tcagcagaag gacattttag gacgggactt gggtgactct agggcactgg 5640
ttttctttcc agagagcgga acaggcgagg aaaagtagtc ccttctcggc gattctgcgg 5700
agggatctcc gtggggcggt gaacgccgat gatgcctcta ctaaccatgt tcatgttttc 5760
tttttttttc tacaggtcct gggtgacgaa cagggtaccg ccaccatggc caccggctct 5820
cgcacaagcc tgctgctggc tttcggactg ctgtgcctgc cttggctcca ggagggctcc 5880
gccgctagca tcgataccgt cgctatgtgc tggaggcttg ctgaaggctg tatgctggac 5940
tatgactcgg gaaatattgt tttggcctct gactgacaat atttcccggt agtcatagtc 6000
caggacacaa ggcctgttac tagcactcac atggaacaaa tggcctctag cctggaggct 6060
tgctgaaggc tgtatgctgg cccacattct agtcttgagt gttttggcct ctgactgaca 6120
ctcaagacta atgaatgtgg gccaggacac aaggcctgtt actagcactc acatggaaca 6180
aatggcctct agcctggagg cttgctgaag gctgtatgct ggaatcgggt agtaagagtg 6240
atgttttggc ctctgactga catcactctt acaatacccg attccaggac acaaggcctg 6300
ttactagcac tcacatggaa caaatggcct ctctagaat 6339

SEQ ID NO: 13 moltype = DNA length = 6339
FEATURE Location/Qualifiers
source 1..6339
mol_type = other DNA
organism = synthetic construct
SEQUENCE: 13 aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc taagcttatc 600
gataccgtcg agatctaact tgtttattgc agcttataat ggttacaaat aaagcaatag 660
catcacaaat ttcacaaata aagcattttt ttcactgcat tctagttgtg gtttgtccaa 720
actcatcaat gtatcttatc atgtctggat ctcgacctcg actagagcat ggctacgtag 780
ataagtagca tggcgggtta atcattaact acaaggaacc cctagtgatg gagttggcca 840
ctccctctct gcgcgctcgc tcgctcactg aggccgggcg accaaaggtc gcccgacgcc 900
cgggctttgc ccgggcggcc tcagtgagcg agcgagcgcg cagctggcgt aatagcgaag 960
aggcccgcac cgatcgccct tcccaacagt tgcgcagcct gaatggcgaa tggcgattcc 1020
gttgcaatgg ctggcggtaa tattgttctg gatattacca gcaaggccga tagtttgagt 1080

```
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
```

```
cgcacaagcc tgctgctggc tttcggactg ctgtgcctgc cttggctcca ggagggctcc  5880
gccgctagca tcgataccgt cgctatgtgc tggaggcttg ctgaaggctg tatgctgtgt  5940
ttagtggctg tgaactcacc gttttggcct ctgactgacg gtgagttcag ccactaaaca  6000
caggacacaa ggcctgttac tagcactcac atggaacaaa tggcctctag cctggaggct  6060
tgctgaaggc tgtatgctga tctttcatcc atcgtaactc ccgttttggc ctctgactga  6120
cgggagttac gggatgaaag atcaggacac aaggcctgtt actagcactc acatggaaca  6180
aatggcctct agcctggagg cttgctgaag gctgtatgct gacatgaatg agaaagttgg  6240
ctccgttttg gcctctgact gacggagcca actctcattc atgtcaggac acaaggcctg  6300
ttactagcac tcacatggaa caaatggcct ctctagaat                         6339

SEQ ID NO: 14          moltype = DNA  length = 6339
FEATURE                Location/Qualifiers
source                 1..6339
                       mol_type = other DNA
                       organism = synthetic construct
SEQUENCE: 14
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
```

```
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgagt  5940
gatatgcgtg cagaacagtc gttttggcct ctgactgacg actgttctgc gcatatcact  6000
caggacacaa ggcctgttac tagcactcac atggaacaaa tggcctctag cctggaggct  6060
tgctgaaggc tgtatgctga ctcaagacta atgaatgtgg gcgttttggc ctctgactga  6120
cgcccacatt ctagtcttga gtcaggacac aaggcctgtt actagcactc acatggaaca  6180
aatggcctct agcctggagg cttgctgaag gctgtatgct gtctattact gcaatcactg  6240
tggcgttttg gcctctgact gacgccacag tgagcagtaa tagacaggac acaaggcctg  6300
ttactagcac tcacatggaa caaatggcct ctctagaat                        6339

SEQ ID NO: 15           moltype = DNA  length = 6339
FEATURE                 Location/Qualifiers
source                  1..6339
                        mol_type = other DNA
                        organism = synthetic construct
SEQUENCE: 15
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
```

-continued

```
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgagg  5940
atagggattg tattggaggc gttttggcct ctgactgacg cctccaataa tccctatcct  6000
caggacacaa ggcctgttac tagcactcac atggaacaaa tggcctctag cctggaggct  6060
tgctgaaggc tgtatgctgt atgaccttct atcttccctc tcgttttggc ctctgactga  6120
cgagagggaa gagaaggtca tacaggacac aaggcctgtt actagcactc acatggaaca  6180
aatggcctct agcctggagg cttgctgaag gctgtatgct gttagtccga aaaatgaggc  6240
tgtcgttttg gcctctgact gacgacagcc tcatttcgga ctaacaggac acaaggcctg  6300
ttactagcac tcacatggaa caaatggcct ctctagaat                        6339
```

SEQ ID NO: 16          moltype = DNA  length = 6339

FEATURE Location/Qualifiers
source 1..6339
mol_type = other DNA
organism = synthetic construct
SEQUENCE: 16 aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc taagcttatc 600
gataccgtcg agatctaact tgtttattgc agcttataat ggttacaaat aaagcaatag 660
catcacaaat ttcacaaata aagcattttt ttcactgcat tctagttgtg gtttgtccaa 720
actcatcaat gtatcttatc atgtctggat ctcgacctcg actagagcat ggctacgtag 780
ataagtagca tggcgggtta atcattaact acaaggaacc cctagtgatg gagttggcca 840
ctccctctct gcgcgctcgc tcgctcactg aggccgggcg accaaaggtc gcccgacgcc 900
cgggctttgc ccgggcggcc tcagtgagcg agcgagcgcg cagctggcgt aatagcgaag 960
aggcccgcac cgatcgccct tcccaacagt tgcgcagcct gaatggcgaa tggcgattcc 1020
gttgcaatgg ctggcggtaa tattgttctg gatattacca gcaaggccga tagtttgagt 1080
tcttctactc aggcaagtga tgttattact aatcaaagaa gtattgcgac aacggttaat 1140
ttgcgtgatg gacagactct tttactcggt ggcctcactg attataaaaa cacttctcag 1200
gattctggcg taccgttcct gtctaaaatc cctttaatcg gcctcctgtt tagctcccgc 1260
tctgattcta acgaggaaag cacgttatac gtgctcgtca aagcaaccat agtacgcgcc 1320
ctgtagcggc gcattaagcg cggcgggtgt ggtggttacg cgcagcgtga ccgctacact 1380
tgccagcgcc ctagcgcccg ctcctttcgc tttcttccct tcctttctcg ccacgttcgc 1440
cggctttccc cgtcaagctc taaatcgggg gctcccttta gggttccgat ttagtgcttt 1500
acggcacctc gaccccaaaa aacttgatta gggtgatggt tcacgtagtg ggccatcgcc 1560
ctgatagacg gtttttcgcc ctttgacgtt ggagtccacg ttctttaata gtggactctt 1620
gttccaaact ggaacaacac tcaaccctat ctcggtctat tcttttgatt tataagggat 1680
tttgccgatt tcggcctatt ggttaaaaaa tgagctgatt taacaaaaat ttaacgcgaa 1740
ttttaacaaa atattaacgt ttacaattta aatatttgct tatacaatct tcctgttttt 1800
ggggcttttc tgattatcaa ccggggtaca tatgattgac atgctagttt tacgattacc 1860
gttcatcgat tctcttgttt gctccagact ctcaggcaat gacctgatag cctttgtaga 1920
gacctctcaa aaatagctac cctctccggc atgaatttat cagctagaac ggttgaatat 1980
catattgatg gtgatttgac tgtctccggc ctttctcacc cgtttgaatc tttacctaca 2040
cattactcag gcattgcatt taaaatatat gagggttcta aaaattttta tccttgcgtt 2100
gaaataaagg cttctcccgc aaaagtatta cagggtcata atgtttttgg tacaaccgat 2160
ttagctttat gctctgaggc tttattgctt aattttgcta attctttgcc ttgcctgtat 2220
gatttattgg atgttggaat tcctgatgcg gtattttctc cttacgcatc tgtgcggtat 2280
ttcacaccgc atatggtgca ctctcagtac aatctgctct gatgccgcat agttaagcca 2340
gccccgacac ccgccaacac ccgctgacgc gccctgacgg gcttgtctgc tcccggcatc 2400
cgcttacaga caagctgtga ccgtctccgg gagctgcatg tgtcagaggt tttcaccgtc 2460
atcaccgaaa cgcgcgagac gaaagggcct cgtgatacgc ctatttttat aggttaatgt 2520
catgataata atggtttctt agacgtcagg tggcactttt cggggaaatg tgcgcggaac 2580
ccctatttgt ttatttttct aaatacattc aaatatgtat ccgctcatga gacaataacc 2640
ctgataaatg cttcaataat attgaaaaag gaagagtatg agtattcaac atttccgtgt 2700
cgcccttatt cccttttttg cggcattttg ccttcctgtt tttgctcacc cagaaacgct 2760
ggtgaaagta aaagatgctg aagatcagtt gggtgcacga gtgggttaca tcgaactgga 2820
tctcaacagc ggtaagatcc ttgagagttt tcgccccgaa gaacgttttc caatgatgag 2880
cacttttaaa gttctgctat gtggcgcggt attatcccgt attgacgccg ggcaagagca 2940
actcggtcgc cgcatacact attctcagaa tgacttggtt gagtactcac cagtcacaga 3000
aaagcatctt acggatggca tgacagtaag agaattatgc agtgctgcca taaccatgag 3060
tgataacact gcggccaact tacttctgac aacgatcgga ggaccgaagg agctaaccgc 3120
ttttttgcac aacatggggg atcatgtaac tcgccttgat cgttgggaac cggagctgaa 3180
tgaagccata ccaaacgacg agcgtgacac cacgatgcct gtagcaatgg caacaacgtt 3240
gcgcaaacta ttaactggcg aactacttac tctagcttcc cggcaacaat taatagactg 3300
gatggaggcg gataaagttg caggaccact tctgcgctcg gcccttccgg ctggctggtt 3360
tattgctgat aaatctggag ccggtgagcg tgggtctcgc ggtatcattg cagcactggg 3420
gccagatggt aagccctccc gtatcgtagt tatctacacg acggggagtc aggcaactat 3480
ggatgaacga aatagacaga tcgctgagat aggtgcctca ctgattaagc attggtaact 3540
gtcagaccaa gtttactcat atatacttta gattgattta aaacttcatt tttaatttaa 3600
aaggatctag gtgaagatcc tttttgataa tctcatgacc aaaatccctt aacgtgagtt 3660
ttcgttccac tgagcgtcag accccgtaga aaagatcaaa ggatcttctt gagatccttt 3720
ttttctgcgc gtaatctgct gcttgcaaac aaaaaaacca ccgctaccag cggtggtttg 3780
tttgccggat caagagctac caactctttt tccgaaggta actggcttca gcagagcgca 3840
gataccaaat actgtccttc tagtgtagcc gtagttaggc caccacttca agaactctgt 3900
agcaccgcct acatacctcg ctctgctaat cctgttacca gtggctgctg ccagtggcga 3960
taagtcgtgt cttaccgggt tggactcaag acgatagtta ccggataagg cgcagcggtc 4020
gggctgaacg gggggttcgt gcacacagcc cagcttggag cgaacgacct acaccgaact 4080
gagataccta cagcgtgagc tatgagaaag cgccacgctt cccgaaggga gaaaggcgga 4140
caggtatccg gtaagcggca gggtcggaac aggagagcgc acgagggagc ttccaggggg 4200
aaacgcctgg tatctttata gtcctgtcgg gtttcgccac ctctgacttg agcgtcgatt 4260
tttgtgatgc tcgtcagggg ggcggagcct atggaaaaac gccagcaacg cggccttttt 4320
acggttcctg gccttttgct ggccttttgc tcacatgttc tttcctgcgt tatcccctga 4380
ttctgtggat aaccgtatta ccgcctttga gtgagctgat accgctcgcc gcagccgaac 4440

```
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg ggggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgatg  5940
acagcctatg tcagagatgc gttttggcct ctgactgacg catctctgat aggctgtcat  6000
caggacacaa ggcctgttac tagcactcac atggaacaaa tggcctctag cctggaggct  6060
tgctgaaggc tgtatgctga ctacttgcat atctcctcac tcgttttggc ctctgactga  6120
cgagtgagga gatgcaagta gtcaggacac aaggcctgtt actagcactc acatggaaca  6180
aatggcctct agcctggagg cttgctgaag gctgtatgct gactgatcta ggaattaggt  6240
acccgttttg gcctctgact gacgggtacc taacctagat cagtcaggac acaaggcctg  6300
ttactagcac tcacatggaa caaatggcct ctctagaat                         6339

SEQ ID NO: 17          moltype = DNA  length = 6339
FEATURE                Location/Qualifiers
source                 1..6339
                       mol_type = other DNA
                       organism = synthetic construct
SEQUENCE: 17
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
```

```
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgtgc  5940
tattagtctg ccatctgtgc gttttggcct ctgactgacg cacagatggg actaatagca  6000
caggacacaa ggcctgttac tagcactcac atggaacaaa tggcctctag cctggaggct  6060
tgctgaaggc tgtatgctgt gtgaaactca atactcagta ccgttttggc ctctgactga  6120
cggtactgag ttgagtttca cacaggacac aaggcctgtt actagcactc acatggaaca  6180
aatggcctct agcctggagg cttgctgaag gctgtatgct gtacatcacc tgaaagtccc  6240
ttgcgttttg gcctctgact gacgcaaggg actcaggtga tgtacaggac acaaggcctg  6300
ttactagcac tcacatggaa caaatggcct ctctagaat                          6339
```

```
SEQ ID NO: 18          moltype = DNA  length = 6340
FEATURE                Location/Qualifiers
source                 1..6340
                       mol_type = other DNA
                       organism = synthetic construct
SEQUENCE: 18
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
```

-continued

```
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
```

-continued ccccaccccc aatttttgtat ttatttattt tttaattatt ttgtgcagcg atgggggcgg 5160
gggggggggg gggcgcgcgc caggcggggc ggggcggggc gaggggcggg gcggggcgag 5220
gcggagaggt gcggcggcag ccaatcagag cggcgcgctc cgaaagtttc cttttatggc 5280
gaggcggcgg cggcggcggc cctataaaaa gcgaagcgcg cggcgggcgg gagtcgctgc 5340
gcgctgcctt cgccccgtgc cccgctccgc cgccgcctcg cgccgcccgc cccggctctg 5400
actgaccgcg ttactaaaac aggtaagtcc ggcctccgcg ccgggttttg gcgcctcccg 5460
cgggcgcccc cctcctcacg gcgagcgctg ccacgtcaga cgaagggcgc agcgagcgtc 5520
ctgatccttc cgcccggacg ctcaggacag cggcccgctg ctcataagac tcggccttag 5580
aaccccagta tcagcagaag gacattttag gacgggactt gggtgactct agggcactgg 5640
ttttctttcc agagagcgga acaggcgagg aaaagtagtc ccttctcggc gattctgcgg 5700
agggatctcc gtggggcggt gaacgccgat gatgcctcta ctaaccatgt tcatgttttc 5760
tttttttttc tacaggtcct gggtgacgaa cagggtaccg ccaccatggc caccggctct 5820
cgcacaagcc tgctgctggc tttcggactg ctgtgcctgc cttggctcca ggagggctcc 5880
gccgctagca tcgataccgt cgctatgtgc tggaggcttg ctgaaggctg tatgctgaag 5940
atgtctgttg tacggtcaac gttttggcct ctgactgacg ttgaccgtaa cagacatctt 6000
caggacacaa ggcctgttac tagcactcac atggaacaaa tggcctctag cctggaggct 6060
tgctgaaggc tgtatgctga ctaactcaag atagctggat tcgttttggc ctctgactga 6120
cgaatccagc tcttgagtta gtcaggacac aaggcctgtt actagcactc acatggaaca 6180
aatggcctct agcctggagg cttgctgaag gctgtatgct gtagaatgca ggaaaccatc 6240
tgtcgttttg gcctctgact gacgacagat ggtcctgcat tctacaggac acaaggcctg 6300
ttactagcac tcacatggaa caaatggcct ctctagaata 6340

SEQ ID NO: 19 moltype = DNA length = 6340
FEATURE Location/Qualifiers
source 1..6340
mol_type = other DNA
organism = synthetic construct
SEQUENCE: 19 aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc taagcttatc 600
gataccgtcg agatctaact tgtttattgc agcttataat ggttacaaat aaagcaatag 660
catcacaaat ttcacaaata aagcattttt ttcactgcat tctagttgtg gtttgtccaa 720
actcatcaat gtatcttatc atgtctggat ctcgacctcg actagagcat ggctacgtag 780
ataagtagca tggcgggtta atcattaact acaaggaacc cctagtgatg gagttggcca 840
ctccctctct gcgcgctcgc tcgctcactg aggccgggcg accaaaggtc gcccgacgcc 900
cgggctttgc ccgggcggcc tcagtgagcg agcgagcgcg cagctggcgt aatagcgaag 960
aggcccgcac cgatcgccct tcccaacagt tgcgcagcct gaatggcgaa tggcgattcc 1020
gttgcaatgg ctggcggtaa tattgttctg gatattacca gcaaggccga tagtttgagt 1080
tcttctactc aggcaagtga tgttattact aatcaaagaa gtattgcgac aacggttaat 1140
ttgcgtgatg gacagactct tttactcggt ggcctcactg attataaaaa cacttctcag 1200
gattctggcg taccgttcct gtctaaaatc cctttaatcg gcctcctgtt tagctcccgc 1260
tctgattcta acgaggaaag cacgttatac gtgctcgtca aagcaaccat agtacgcgcc 1320
ctgtagcggc gcattaagcg cggcgggtgt ggtggttacg cgcagcgtga ccgctacact 1380
tgccagcgcc ctagcgcccg ctcctttcgc tttcttccct tcctttctcg ccacgttcgc 1440
cggctttccc cgtcaagctc taaatcgggg gctcccttta gggttccgat ttagtgcttt 1500
acggcacctc gaccccaaaa aacttgatta gggtgatggt tcacgtagtg ggccatcgcc 1560
ctgatagacg gtttttcgcc ctttgacgtt ggagtccacg ttctttaata gtggactctt 1620
gttccaaact ggaacaacac tcaaccctat ctcggtctat tcttttgatt tataagggat 1680
tttgccgatt tcggcctatt ggttaaaaaa tgagctgatt taacaaaaat ttaacgcgaa 1740
ttttaacaaa atattaacgt ttacaattta aatatttgct tatacaatct tcctgttttt 1800
ggggcttttc tgattatcaa ccggggtaca tatgattgac atgctagttt tacgattacc 1860
gttcatcgat tctcttgttt gctccagact ctcaggcaat gacctgatag cctttgtaga 1920
gacctctcaa aaatagctac cctctccggc atgaatttat cagctagaac ggttgaatat 1980
catattgatg gtgatttgac tgtctccggc ctttctcacc cgtttgaatc tttacctaca 2040
cattactcag gcattgcatt taaaatatat gagggttcta aaaattttta tccttgcgtt 2100
gaaataaagg cttctcccgc aaaagtatta cagggtcata atgtttttgg tacaaccgat 2160
ttagctttat gctctgaggc tttattgctt aatttttgcta attctttgcc ttgcctgtat 2220
gatttattgg atgttggaat tcctgatgcg gtattttctc cttacgcatc tgtgcggtat 2280
ttcacaccgc atatggtgca ctctcagtac aatctgctct gatgccgcat agttaagcca 2340
gccccgacac ccgccaacac ccgctgacgc gccctgacgg gcttgtctgc tcccggcatc 2400
cgcttacaga caagctgtga ccgtctccgg gagctgcatg tgtcagaggt tttcaccgtc 2460
atcaccgaaa cgcgcgagac gaaagggcct cgtgatacgc ctatttttat aggttaatgt 2520
catgataata atggtttctt agacgtcagg tggcactttt cggggaaatg tgcgcggaac 2580
ccctatttgt ttatttttct aaatacattc aaatatgtat ccgctcatga gacaataacc 2640
ctgataaatg cttcaataat attgaaaaag gaagagtatg agtattcaac atttccgtgt 2700
cgcccttatt cccttttttg cggcattttg ccttcctgtt tttgctcacc cagaaacgct 2760
ggtgaaagta aaagatgctg aagatcagtt gggtgcacga gtgggttaca tcgaactgga 2820
tctcaacagc ggtaagatcc ttgagagttt tcgccccgaa gaacgttttc caatgatgag 2880
cacttttaaa gttctgctat gtggcgcggt attatcccgt attgacgccg ggcaagagca 2940
actcggtcgc cgcatacact attctcagaa tgacttggtt gagtactcac cagtcacaga 3000
aaagcatctt acggatggca tgacagtaag agaattatgc agtgctgcca taaccatgag 3060

-continued tgataacact gcggccaact tacttctgac aacgatcgga ggaccgaagg agctaaccgc 3120
tttttgcac aacatggggg atcatgtaac tcgccttgat cgttgggaac cggagctgaa 3180
tgaagccata ccaaacgacg agcgtgacac cacgatgcct gtagcaatgg caacaacgtt 3240
gcgcaaacta ttaactggcg aactacttac tctagcttcc cggcaacaat taatagactg 3300
gatggaggcg gataaagttg caggaccact tctgcgctcg gcccttccgg ctggctggtt 3360
tattgctgat aaatctggag ccggtgagcg tgggtctcgc ggtatcattg cagcactggg 3420
gccagatggt aagccctccc gtatcgtagt tatctacacg acggggagtc aggcaactat 3480
ggatgaacga aatagacaga tcgctgagat aggtgcctca ctgattaagc attggtaact 3540
gtcagaccaa gtttactcat atatacttta gattgattta aaacttcatt tttaatttaa 3600
aaggatctag gtgaagatcc tttttgataa tctcatgacc aaaatccctt aacgtgagtt 3660
ttcgttccac tgagcgtcag accccgtaga aaagatcaaa ggatcttctt gagatccttt 3720
ttttctgcgc gtaatctgct gcttgcaaac aaaaaaacca ccgctaccag cggtggtttg 3780
tttgccggat caagagctac caactctttt tccgaaggta actggcttca gcagagcgca 3840
gataccaaat actgtccttc tagtgtagcc gtagttaggc caccacttca agaactctgt 3900
agcaccgcct acatacctcg ctctgctaat cctgttacca gtggctgctg ccagtggcga 3960
taagtcgtgt cttaccgggt tggactcaag acgatagtta ccggataagg cgcagcggtc 4020
gggctgaacg gggggttcgt gcacacagcc cagcttggag cgaacgacct acaccgaact 4080
gagataccta cagcgtgagc tatgagaaag cgccacgctt cccgaaggga gaaaggcgga 4140
caggtatccg gtaagcggca gggtcggaac aggagagcgc acgagggagc ttccaggggg 4200
aaacgcctgg tatctttata gtcctgtcgg gtttcgccac ctctgacttg agcgtcgatt 4260
tttgtgatgc tcgtcagggg ggcggagcct atggaaaaac gccagcaacg cggccttttt 4320
acggttcctg gccttttgct ggccttttgc tcacatgttc tttcctgcgt tatcccctga 4380
ttctgtggat aaccgtatta ccgcctttga gtgagctgat accgctcgcc gcagccgaac 4440
gaccgagcgc agcgagtcag tgagcgagga agcggaagag cgcccaatac gcaaaccgcc 4500
tctccccgcg cgttggccga ttcattaatg cagcagctgc gcgctcgctc gctcactgag 4560
gccgcccggg caaagcccgg gcgtcgggcg acctttggtc gcccggcctc agtgagcgag 4620
cgagcgcgca gagagggagt ggccaactcc atcactaggg gttccttgta gttaatgatt 4680
aacccgccat gctacttatc tacgtagcca tgctctagga cattgattat tgactagtgg 4740
agttccgcgt tacataactt acggtaaatg gcccgcctgg ctgaccgccc aacgaccccc 4800
gcccattgac gtcaataatg acgtatgttc ccatagtaac gccaataggg actttccatt 4860
gacgtcaatg ggtggagtat ttacggtaaa ctgcccactt ggcagtacat caagtgtatc 4920
atatgccaag tacgccccct attgacgtca atgacggtaa atggcccgcc tggcattatg 4980
cccagtacat gaccttatgg gactttccta cttggcagta catctacgta ttagtcatcg 5040
ctattaccat ggtcgaggtg agccccacgt tctgcttcac tctccccatc tcccccccct 5100
ccccaccccc aattttgtat ttatttattt tttaattatt ttgtgcagcg atgggggcgg 5160
gggggggggg ggggcgcgcgc caggcggggc ggggcggggc gaggggcggg gcggggcgag 5220
gcggagaggt gcggcggcag ccaatcagag cggcgcgctc cgaaagtttc cttttatggc 5280
gaggcggcgg cggcggcggc cctataaaaa gcgaagcgcg cggcgggcgg gagtcgctgc 5340
gcgctgcctt cgccccgtgc cccgctccgc cgccgcctcg cgccgcccgc cccggctctg 5400
actgaccgcg ttactaaaac aggtaagtcc ggcctccgcg ccgggttttg gcgcctcccg 5460
cgggcgcccc cctcctcacg gcgagcgctg ccacgtcaga cgaagggcgc agcgagcgtc 5520
ctgatccttc cgcccggacg ctcaggacag cggcccgctg ctcataagac tcggccttag 5580
aaccccagta tcagcagaag gacattttag gacgggactt gggtgactct agggcactgg 5640
ttttctttcc agagagcgga acaggcgagg aaaagtagtc ccttctcggc gattctgcgg 5700
agggatctcc gtggggcggt gaacgccgat gatgcctcta ctaaccatgt tcatgttttc 5760
tttttttttc tacaggtcct gggtgacgaa cagggtaccg ccaccatggc caccggctct 5820
cgcacaagcc tgctgctggc tttcggactg ctgtgcctgc cttggctcca ggagggctcc 5880
gccgctagca tcgataccgt cgctatgtgc tggaggcttg ctgaaggctg tatgctgtac 5940
tgttcgacct gtcacatcat cgttttggcc tctgactgac gatgatgtga ggtcgaacag 6000
tcaggacaca aggcctgtta ctagcactca catggaacaa atggcctcta gcctggaggc 6060
ttgctgaagg ctgtatgctg tctgttgacg tatcgtgatc tgcgttttgg cctctgactg 6120
acgcagatca cgacgtcaac agacaggaca caaggcctgt tactagcact cacatggaac 6180
aaatggcctc tagcctggag gcttgctgaa ggctgtatgc tgtgagtgta atgaacagtt 6240
ggcacgtttt ggcctctgac tgacgtgcca actgcattac actcacagga cacaaggcct 6300
gttactagca ctcacatgga acaaatggcc tctctagaat 6340

SEQ ID NO: 20 moltype = DNA length = 6339
FEATURE Location/Qualifiers
source 1..6339
mol_type = other DNA
organism = synthetic construct
SEQUENCE: 20
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc taagcttatc 600
gataccgtcg agatctaact tgtttattgc agcttataat ggttacaaat aaagcaatag 660
catcacaaat ttcacaaata aagcattttt ttcactgcat tctagttgtg gtttgtccaa 720
actcatcaat gtatcttatc atgtctggat ctcgacctcg actagagcat ggctacgtag 780
ataagtagca tggcgggtta atcattaact acaaggaacc cctagtgatg gagttggcca 840
ctccctctct gcgcgctcgc tcgctcactg aggccgggcg accaaaggtc gcccgacgcc 900
cgggctttgc ccgggcggcc tcagtgagcg agcgagcgcg cagctggcgt aatagcgaag 960
aggcccgcac cgatcgccct tcccaacagt tgcgcagcct gaatggcgaa tggcgattcc 1020

-continued

```
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aatttttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgccccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
```

```
ttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgtaa  5940
atttcccttg gctgcaaggc gttttggcct ctgactgacg ccttgcagca gggaaattta  6000
caggacacaa ggcctgttac tagcactcac atggaacaaa tggcctctag cctggaggct  6060
tgctgaaggc tgtatgctga gtttagcttg atgaaagatc ccgttttggc ctctgactga  6120
cgggatcttt ccaagctaaa ctcaggacac aaggcctgtt actagcactc acatggaaca  6180
aatggcctct agcctggagg cttgctgaag gctgtatgct gacttaaatc agaagtcctc  6240
ctccgttttg gcctctgact gacggaggag gacctgattt aagtcaggac acaaggcctg  6300
ttactagcac tcacatggaa caaatggcct ctctagaat                          6339

SEQ ID NO: 21          moltype = DNA  length = 6341
FEATURE                Location/Qualifiers
source                 1..6341
                       mol_type = other DNA
                       organism = synthetic construct
SEQUENCE: 21
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
```

-continued

```
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgggt  5940
gaaggaggat cgcctagaag ttttggcctc tgactgacta aaatttccct gtgctgcaag  6000
gacaggacac aaggcctgtt actagcactc acatggaaca aatggcctct agcctggagg  6060
cttgctgaag gctgtatgct gggaggagga cctgatttaa gtgttttggc ctctgactga  6120
cacttaaatc agatgtcctc ctcccaggac acaaggcctg ttactagcac tcacatggaa  6180
caaatggcct ctagcctgga ggcttgctga aggctgtatg ctgggtgaag gaggatcgct  6240
agaagttttg gcctctgact gacttctagc gatcaactcc ttcacccagg acacaaggcc  6300
tgttactagc actcacatgg aacaaatggc ctctctagaa t                      6341
```